US007822219B2

(12) United States Patent
Baker et al.

(10) Patent No.: US 7,822,219 B2
(45) Date of Patent: Oct. 26, 2010

(54) CARTILAGE DISPLACING BEAD, RIDGE, OR KEY PROJECTION

(76) Inventors: Lawrence K. Baker, 193 Cypress St., Gate City, VA (US) 24251; John G. Casali, 3003 Tall Oaks Dr., Blacksburg, VA (US) 24060

( * ) Notice: Subject to any disclaimer, the term of this patent is extended or adjusted under 35 U.S.C. 154(b) by 253 days.

(21) Appl. No.: 12/143,090

(22) Filed: Jun. 20, 2008

(65) Prior Publication Data

US 2009/0154748 A1 Jun. 18, 2009

Related U.S. Application Data

(60) Provisional application No. 60/936,492, filed on Jun. 20, 2007.

(51) Int. Cl.

| | |
|---|---|
| ***H04R 25/00*** | (2006.01) |
| *H04R 25/02* | (2006.01) |
| *A61F 11/00* | (2006.01) |
| *B21F 43/00* | (2006.01) |

(52) U.S. Cl. ........................ 381/328; 381/380; 181/130; 128/864; 29/896.21

(58) Field of Classification Search ................. 381/322, 381/327-328, 330, 380-381; 181/128-135; 128/857, 864-865, 867; 29/896.21
See application file for complete search history.

(56) References Cited

U.S. PATENT DOCUMENTS 6,940,988 B1 * 9/2005 Shennib et al. ............. 381/322
2006/0050914 A1 * 3/2006 Urso et al. .................. 381/328
2006/0067551 A1 * 3/2006 Cartwright et al. .......... 381/322

* cited by examiner

*Primary Examiner*—Brian Ensey
*Assistant Examiner*—Sunita Joshi
(74) *Attorney, Agent, or Firm*—John P. Keady

(57) ABSTRACT

At least one exemplary embodiment is directed to an in-the-ear-canal device comprising: an insertion element; and at least one non-circumferential protrusion, where the at least one non-circumferential protrusion is operatively connected to a surface of the insertion element and provides a stabilizing force for maintaining the position of the insertion element in an ear canal.

10 Claims, 4 Drawing Sheets sideview sideview

CARTILAGE DISPLACING BEAD, RIDGE, OR KEY PROJECTION

CROSS-REFERENCE TO RELATED APPLICATIONS

This application claims the benefit of U.S. provisional patent application No. 60/936,492 filed on 20 Jun. 2007. The disclosure of which is incorporated herein by reference in its entirety.

FIELD OF THE INVENTION

The present invention relates to earpieces and more particular, though not exclusively, to protrusions on earpieces for cartilage displacement.

BACKGROUND OF THE INVENTION

Cartilaginous anatomical structures of the human body have a compliancy and malleability that, at least in some of those structures, allow the cartilage to be compressed, displaced, or otherwise temporarily altered in shape, without injury, by the application of an externally-applied object to said cartilaginous structure.

It is opportune that earpieces can be used in the ear canal because of the human tissue materials comprising the outer portion of the ear canal wall (i.e., that which is proximal to the ear canal rim or opening); this tissue being flesh over cartilage for up to about one-half of the total depth of the ear canal (and then being flesh over bone for approximately the inner half of the total depth). As such, most ear canal insert devices will engage at least the cartilaginous region, and may extend into the bony-walled region.

In current practice, an attempt is made to reduce movement of ear inserts, such as hearing aids, and loss of acoustic seal by molding custom-molded ear inserts or hearing aids as slightly oversized (larger) than the ear impression obtained on the user, and this oversizing is generally achieved along the full surface area of the insert. Another current practice technique is to add one or more ring-shaped projections or attachments, such as an O-ring, which encircle the insert around its cross-section. However, while either of these approaches may offer some resistance to the insert moving backward out of the ear, neither prevents the insert from moving in the yaw or roll axes as described above, and neither provides an effective countermeasure against the loss of seal which can readily occur during jaw movements. For example, the ring projection does not help in reducing yaw motions because the ring acts as a pivot point about which the earplug can wobble, and it does not help in roll because it establishes no edge against the ear canal walls in the cross-sectional direction. Furthermore, both the oversized ear impression and the ring approaches may result in pain because the ear canal is essentially "stretched" over a substantial portion of its surface. It is also important to recognize that a uniformly oversized hearing aid engages the compliant, cartilaginous portion of the ear canal in a uniform manner, thus being free to "float" within the ear canal cavity, thereby responding to jaw movement by moving itself, thereby being rendered as physically unstable in the canal and losing its acoustic seal. Furthermore, a common occurrence with a hearing aid wherein a loss of seal is experienced is acoustic feedback between the external microphone and the receiver loudspeaker which the external microphone then acoustically confronts due to the loss of seal that separates the two. This feedback is typically heard as an audible "squeal," and is objectionable to both the user and others in the vicinity.

In addition to ring projection systems, several related art systems use a trench vent and/or a duct ven, the purpose of which is to form a pathway through which air (and thus sound) can pass, being advantageous for improving the acoustic response of the hearing device, and for reducing the objectionable "occlusion" effect which manifests as the user's voice sounding bassy and resonant to himself or herself.

SUMMARY OF THE INVENTION

At least one exemplary embodiment is directed to a means (e.g., longitudinal ridge or protrusion) of displacing cartilage, and to some extent the dermis covering it, with a preformed surface of an object applied to it (e.g., a protrusion), for example configured to engage the object with the cartilaginous anatomical region, and in some instances, holding and stabilizing that object in place against the bodily region.

At least one exemplary embodiment is directed to a method of cartilage displacement on the body and can include various and multiple bodily locations, for example a readily understood, and much-needed application concerns the design of in-ear canal "inserts," such as hearing aids, earplugs, earphones for music or other content rendition, and other ear canal-seated, hereafter "insert," devices. Although hearing aids are referred to as illustrative examples, the present invention is applicable to insertion elements (e.g., hearing aids, earplugs, earphones, earbuds, and other ear insertable devices as known by one of ordinary skill in the relevant art). Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limited the scope of the invention.

At least one exemplary embodiment is directed to a method that displaces a cartilaginous structure and due to the fact that the cartilaginous structure has compliance and deformability, it can be exploited as an opportunity for a suitably formed hearing aid device to displace, by creating a depression, the cartilage, which, in effect, will enable the insert to be securely held in place, stabilized, and in some applications, improve the seal of a hearing aid or other ear insert.

At least one exemplary embodiment is directed to a cartilage-displacing longitudinal projection on the surface of a device that is designed to interface with the human body in a region of the body in which the flesh has underlying cartilaginous structure, of which the outer portion of the ear canal is a prime example.

At least one further exemplary embodiment is directed to displacing the cartilage, which it engages by a volume and a shape, which are both approximately equivalent to the volume and shape of the projection (e.g., protrusion). In effect, the projection will act as a key, which displaces the cartilage, which temporarily while being confronted by the projection, forms a keyway.

At least one further exemplary embodiment utilizes the cartilage-displacing projection to facilitate securely locate, hold in place, and create and maintain a seal of the device, such as a hearing aid, against the flesh over the cartilage that is displaced.

By facilitating the maintaining of the proper position of the device, exemplary embodiments of this invention serve to improve the user's comfort and acceptability of the ear insert device, such as a hearing aid.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS OF THE PRESENT INVENTION

Figure 1:
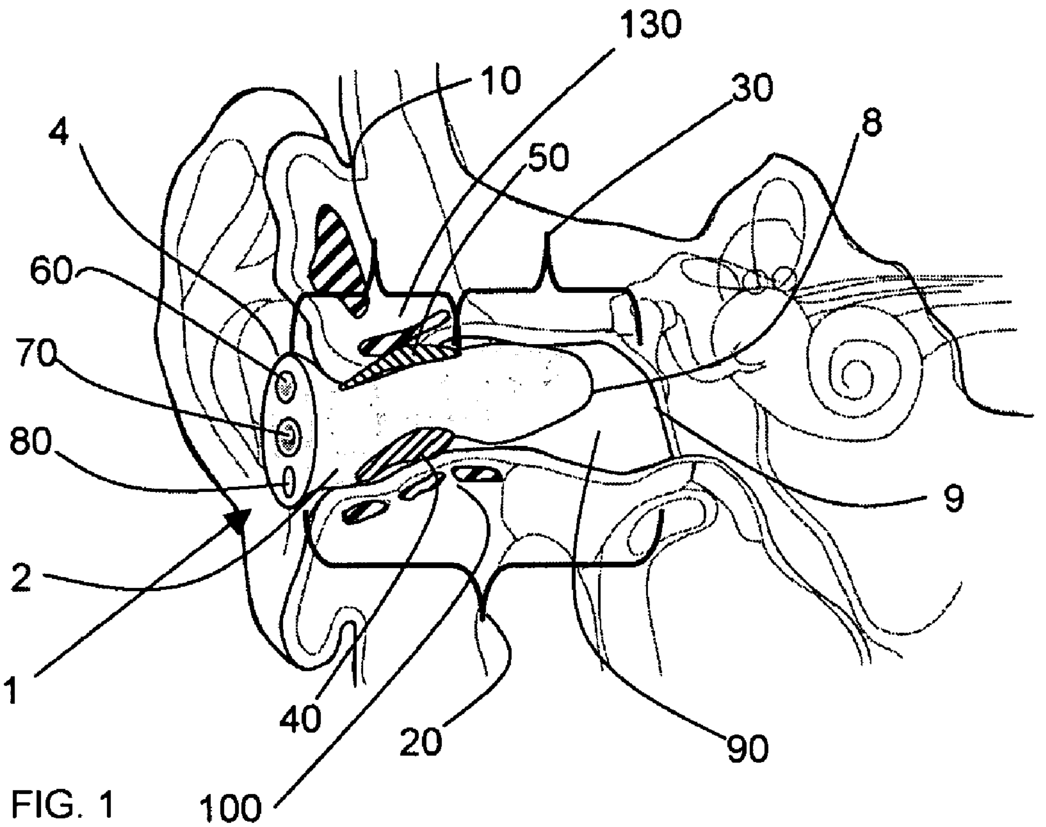
FIG. 1 is a frontal view in the coronal plane view of a person's right outer ear and ear canal as fitted with a hearing aid comprising a custom-molded hearing aid that fits within the ear canal.

The following description of exemplary embodiment(s) is merely illustrative in nature and is in no way intended to limit the invention, its application, or uses.

Exemplary embodiments are directed to or can be operatively used on various wired or wireless earpiece devices (e.g., earbuds, headphones, ear terminal, hearing aids, behind the ear devices, or other acoustic devices as known by one of ordinary skill in the art, and equivalents).

Processes, techniques, apparatus, and materials as known by one of ordinary skill in the art may not be discussed in detail but are intended to be part of the enabling description where appropriate. For example material fabrication may not be disclosed, nor attachment procedures (e.g., adhesive attaching of separate ridge structures), but such, as known by one of ordinary skill in such arts is intended to be included in the discussion herein when necessary.

Notice that similar reference numerals and letters refer to similar items in the following figures, and thus once an item is defined in one figure, it may not be discussed or further defined in the following figures.

The aforesaid displacement of cartilage has, for example, major implications for improving the fit, security, seal, and stability of custom-molded hearing aids or earplugs, as they are currently designed, which now "float" as in the ear canal in the sense that they do not displace cartilage in a specific region. The ear canal cartilage can be described as a semi-fluid, such as a high-viscosity gel, and as such, the cartilage-engaging hearing aid or earplug readily "rolls" around its longitudinal axis and/or "yaws" around any axis projecting through its cross-section, especially when the ear canal exhibits dynamic distortion due to chewing, talking, or coughing, and/or when the head exhibits rapid angular movements or is subjected to external forces. As a result, the conventional custom-molded hearing aid or earplug moves or "floats" differentially to the ear canal, resulting in loss of acoustic seal, partial dislodging of the insert, and even the insert falling out of the ear. Furthermore, a common occurrence with a hearing aid wherein a loss of seal is experienced due to this phenomena is acoustic feedback between the external microphone and the receiver loudspeaker which the external microphone then acoustically confronts due to the loss of seal that separates the two. This feedback is typically heard as an audible "squeal," and is objectionable to both the user and others in the vicinity.

In at least one exemplary embodiment, along a portion of the length of the ear canal insert, a single bead projection or a series of multiple bead projections are added to the insert's surface in a linear fashion along a portion of the length of the insert. These beads may be of various cross-sectional geometries such as hemispheres, triangles, inverted cups, etc., and can be produced as discrete multiple beads, or as single elongated bead or "ridge" that run along a portion of the length of the insert in similar fashion to a welder's bead of melted welding rod that runs along a length of metal. By adding such a longitudinal bead-type projection to a custom-molded hearing aid or earplug, the cartilage of the ear canal, which is engaged, upon insertion of the hearing aid, by that projection will be displaced; in essence the bead will serve as a key, and the displaced cartilage will result in a keyway. Thus, the problems of the ear canal insert (or any other cartilage-engaging object for that matter) which are manifested as yawing, rolling, and/or dislodging from the anatomical structure which it engages, will be greatly inhibited due to the fact that the hearing aid includes an integral key, i.e., the bead/ridge projection, which then creates a keyway in the cartilage upon insertion. Continuing with the fluid analogy of the cartilage mentioned earlier, a projecting, longitudinal bead/ridge has the same effect on the ear canal insert as does a keel running longitudinally along the bottom of the hull of a boat—it reduces the tendency of rolling about a longitudinal axis and yawing about a vertical axis, or for that matter, yawing about any axis that projects though the cross-section of the insert. Furthermore, it will be recognized that In the specific applications of a custom-molded hearing aid or earplug, such a ridge is relatively comfortable and is easily adjusted in height depending upon the particular wearer's need and comfort by means of a bench grinder for reduction or addition of acrylic or other material for addition. This enables in-office alterations to be made easily by the hearing aid or earplug dispensing professional in the same manner of a dental adjustment by a dentist for dentures.

Different applications of the herein-described method of cartilage displacement on the body will be obvious to a person having ordinary skill in the art; however, an exemplary embodiment described next concerns the design of in-ear hearing aids of the type that are custom-molded for the individual user.

Referring now to the figures, FIG. 1 illustrates a custom-fitted, in-the-ear hearing aid 1 of the in-the-canal type, which is a popular configuration of modern hearing aids. The shell/housing 2, which forms the surface of the hearing aid, is replicated from an ear impression that is prior obtained via the use of an impression material in its viscous state having been injected into the ear canal 90 of the user. Therefore, hearing aid shell 2 conforms to the ear canal shape of said user. At the auricular (external) end 4 of the hearing aid is typically located the volume control 70, the microphone 60, and the battery 80. At the opposite, internal end 8 (toward the tympanum or eardrum 9), is a sound output port through which amplified sound exits near the tympanum.

In anatomical terms, the auricular end 4 of a hearing aid has a generally oval (elliptical) shape and size, which mimics the wall shape and circumference of the outer, cartilaginous portion 10 of the ear canal 90 of the user. The major axis of the oval tends to be vertical at the auricular, cartilaginous end, but in some ear canals, this major axis rotates toward the horizontal as it approaches the tympanum 9, in the bony region 30 of the ear canal 90. In at least one exemplary embodiment, at either or both ends of the major axis along the length of the hearing aid which engages the cartilaginous region 10 of the ear canal, projections, also known as ridges, beads, or keys 40&50 from the otherwise oval body of the canal type hearing aid 1 are added. These projections 40&50 run lengthwise (longitudinally) along the apex of one or both ends of the major axis, and their lengths will be dependent upon the needs of the individual fitting. (It is also possible to position these projections at other axial locations on the shell/housing 2 of the hearing aid than at the apex of the major axis, though in most users the apex is an optimal location.) These ridge/key projections 40&50, in performing one of their intended functions (stabilizing the hearing aid in the ear canal 90), are essentially a type of key device which, when inserted into the ear canal 90 as an integral part of the hearing aid, slide into the subdermal troughs 100 & 130 thereby displacing the compliant tissue and cartilage in the outer portion 10 of the ear canal 90. Thus, the ridge or "key" 40&50 interlocks with the trough "keyway" that is created by displacement of the underlying cartilage, providing a mechanism for locking, and thereby stabilizing, the hearing aid 1 in the ear canal 90. In this manner, the hearing aid 1 is inhibited from rolling in the ear canal about an axis running through the cross-section of the hearing aid 1, yawing in the ear canal about an axis running longitudinally through the length of the hearing aid 1, and from backing out longitudinally from the ear canal 90. This has advantages in that the hearing aid 1 retains its fit, does not feel to the user as if it is wobbling or otherwise loose, and because it remains securely in place, may reduce irritation due to dislocation of the hearing aid 1.

Another function provided by this ridge/key design is that it improves the acoustic seal that is important to the performance of the hearing aid. An acoustic seal is important to prevent the audible squeal that occurs when the hearing aid's microphone 60 is exposed to the output of a sound port, constituting a feedback situation. Also, the acoustic seal helps to provide attenuation of external noises, these noises constituting a source of interference with the audibility of desirable signals and human speech. The acoustic seal's integrity is dependent in large part upon the contact between the hearing aid's outer surface and the ear canal's wall. The fact that the ridge/key 40&50 establishes a secure interlock with the cartilaginous trough "keyway" facilitates this seal via two mechanisms: 1) it tightens (stretches) the dermis of the outer ear canal wall, thereby increasing the pressure between the skin and hearing aid's outer surface, and 2) it inhibits movement (including roll, yaw, and backing out of the canal) of the hearing aid 1 in the ear canal 90, thereby helping to maintain an acoustic seal under dynamic conditions. One problem that is addressed by both of these benefits of the ridge/key projection is that posed by the stimulus which is produced by opening and closing of the temporomandibular joint (TMJ), such as during talking or chewing, which tends to break the seal between the hearing aid 1 and canal walls and/or to cause the hearing aid to move around in the ear canal 90. The existence of the ridge(s) 40&50 will help to minimize these effects of TMJ movement on hearing aid movement and loss of seal. Furthermore, some users may experience relief from mild cases of TMJ-induced and similar pain in that the ridge key system helps to stabilize and support the joint during movement in some individuals.

Figure 2:
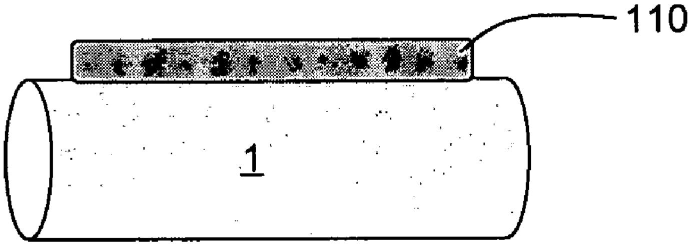
FIGS. 2-8 are various side-views and end-views of an hearing aid showing various ridge/key projections having different locations and cross-sectional geometric shapes in each figure.
Figure 3:
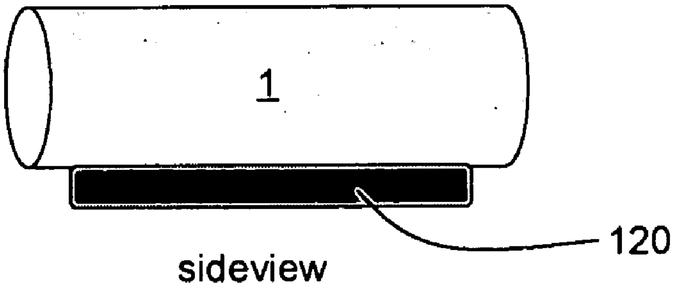
Figure 4:
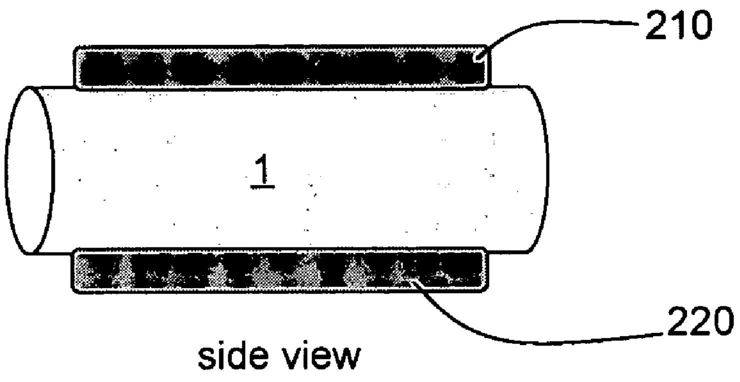
Figure 5:
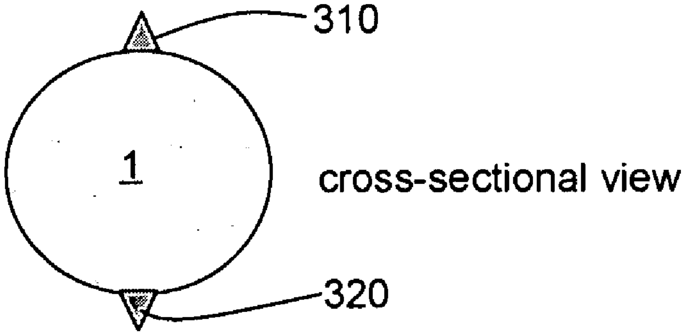
Figure 6:
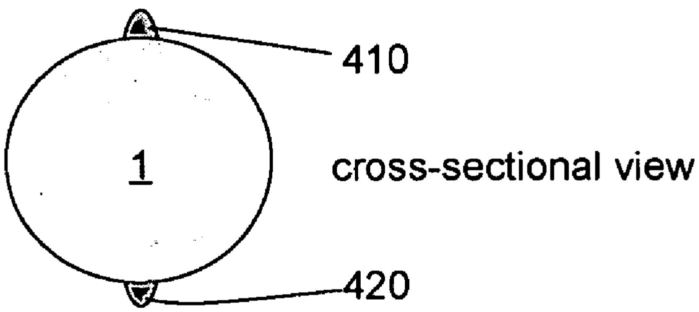
Figure 7:
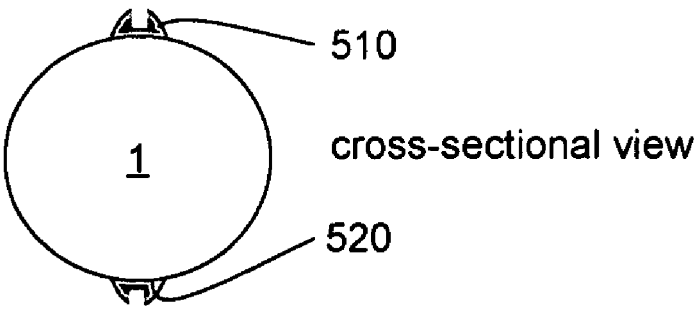
Figure 8:
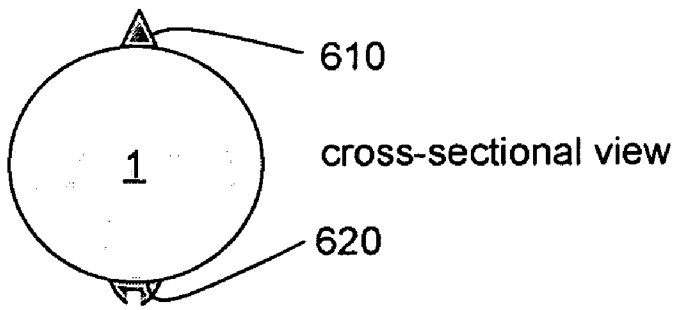

Alternative designs for the ridge/key projections on hearing aids or other hearing aid devices can be produced in various forms, and are readily formed with various polymers or other materials into different geometric shapes and sizes. FIG. 2 depicts a longitudinal ridge/key projection 110 along the bottom of the hearing aid 1, which will produce a displacement of cartilage in the form of a keyway along the ear canal's floor. FIG. 3 depicts a longitudinal ridge/key projection 120 along the top of the ear insert 1 (e.g., hearing aid), which will produce a displacement of cartilage in the form of a keyway along the ear canal's roof. FIG. 4 depicts a duality of longitudinal ridge/key projections 210 and 220 along both the top and bottom of the ear insert 1, which will produce displacements of cartilage in the form of keyways along the ear canal's roof and floor. FIGS. 5, 6, 7, and 8 all depict various cross-sectional geometries of projections for the ridge/keys 310, 320, 410, 420, 510, 520, 610, and 620 that run along a portion of the length of the ear insert 1, said geometries consisting of triangular, round, grooved, and combinations thereof, respectively in the figures.

Projection for Mandibular Joint Embodiment

Figure 9:
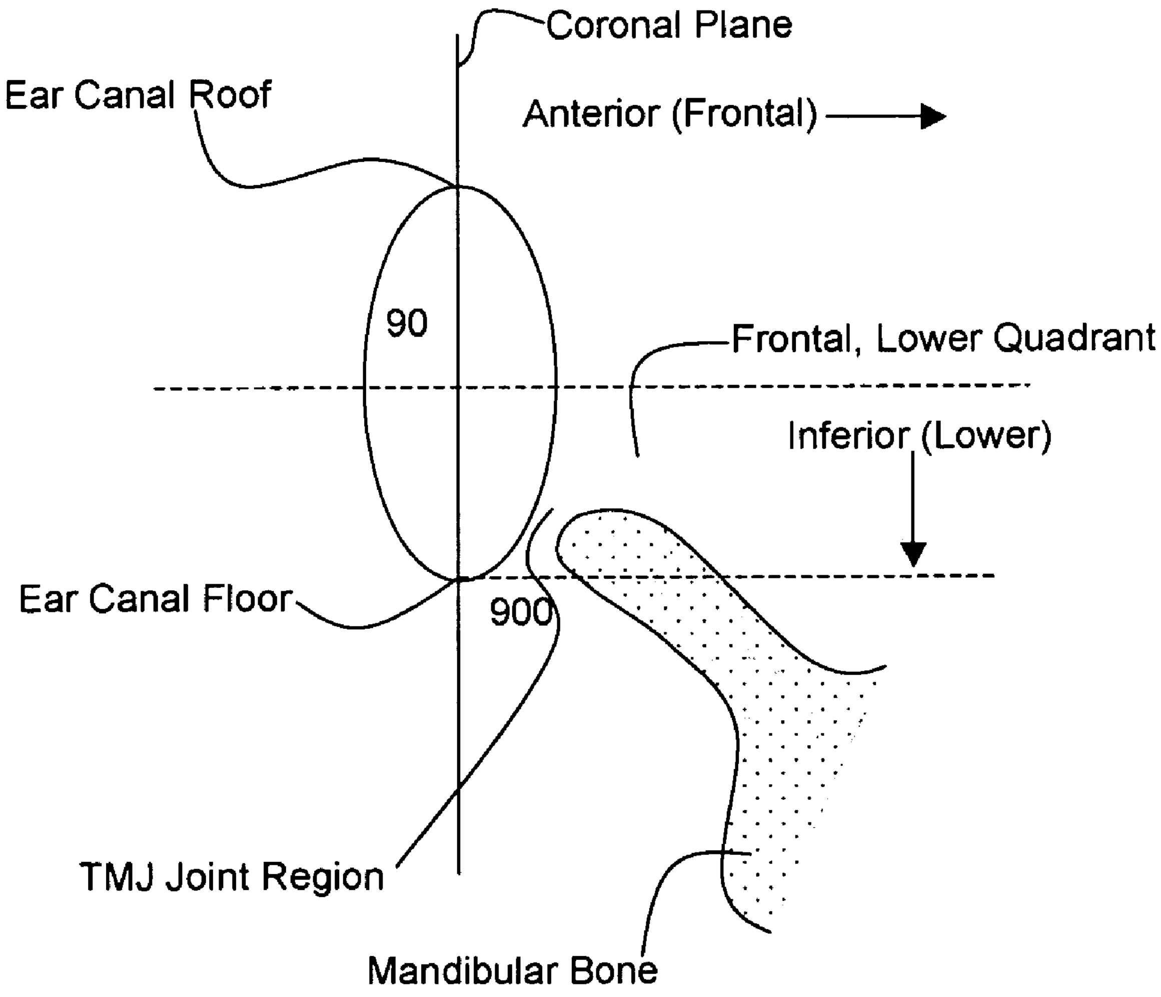
FIG. 9 is a cross-sectional side view of a person's ear canal in proximity to the terminus of the mandibular bone at the temporomandibular joint (TMJ)
Figure 10:
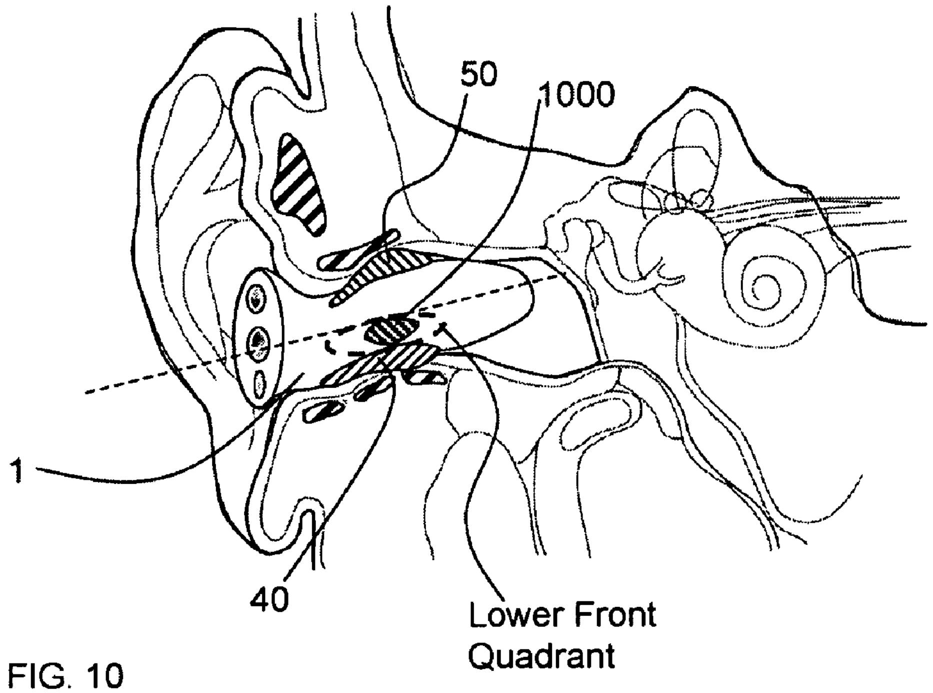
FIG. 10 is a frontal perspective, saggital plane view of a person's right ear canal as fitted with a hearing aid comprising a custom-molded hearing aid that fits within the ear canal, said insert including longitudinal ridge/key projections on the upper and lower surfaces, combined with another shorter projection to apply pressure to the mandibular bone at the temporomandibular joint (TMJ)

A further embodiment of the present invention is to provide a feature which helps prevent the temporomandibular joint (TMJ) or hinge, depicted as 900 in FIG. 9, from distorting the ear canal 90 by applying pressure against the TMJ which "pushes back" on the joint in a direction that is away from the ear canal 90 during joint movement. As depicted in FIG. 10, this feature comprises a projection 1000 for confronting the TMJ at the lower (interior) front (anterior) quadrant of the hearing aid 1, said projection's purpose being to "push back" against the mandibular hinge to help minimize shifting of the TMJ during opening/closing of the jaw. The height of the projection 1000 can be approximately 0.040-inch or more, depending upon the needs of the user. Since a major aspect of the invention is adjustability—the "TMJ projection" can be honed down or increased in size by the addition of more material, as needed, on site. The invention relies upon the prior discussed longitudinal ridge/key feature, shown as 40 and/or 50 in FIG. 10, which maintains stability of the hearing aid 1 in the car canal 90 during TMJ movement, while the additional "TMJ projection" 1000 which applies pressure against the TMJ helps to stabilize the joint. The effectiveness of the TMJ projection is dependent upon the hearing aid remaining as locked in place in the ear canal as accomplished by the ridge/key projection(s) 40 and/or 50.

Projection for Venting Embodiment

It is well known in hearing aid design, and in some instances of other ear insert device designs such as earphones for communications, that the inclusion of a pathway through which air (and thus sound) can pass, is advantageous for improving the acoustic response of the hearing device, and for reducing the objectionable "occlusion" effect which manifests as the user's voice sounding bassy and resonant to himself or herself. In this regard, the related art utilizes venting, which consists either of a duct vent drilled or formed through the body of a hearing aid, or alternatively, as a "trench or groove" that is formed (recessed) into the surface of a hearing aid. Smaller hearing aids, especially those of the completely-in-the-canal type, are especially limited as to the size of the vent that can be accomplished, due to the fact that such devices are packed with electronics. In some users, it is advantageous to include a vent whose opening is as large as possible, and with the current duct and trench vents, vent opening size is constrained by the cross-sectional area of the hearing aid.

Figure 11:
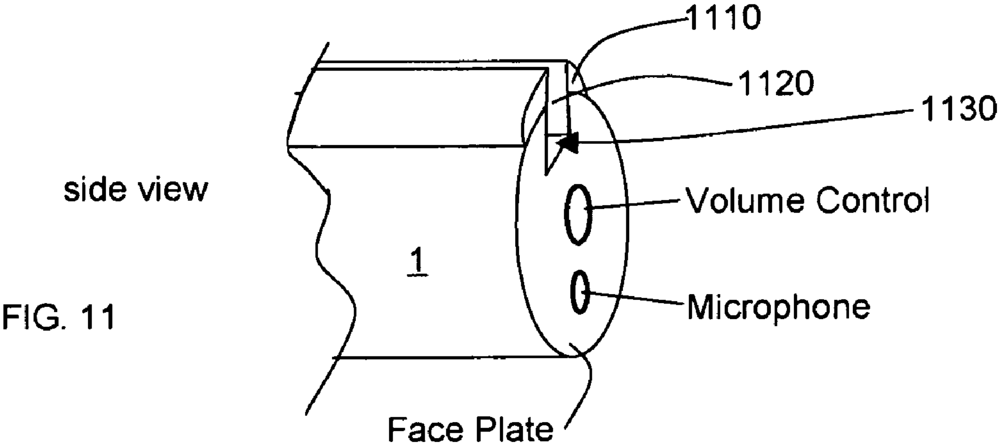
FIG. 11 is a side and end view of the present invention's ridge/key projection depicting its application in providing an trench-type enhancement or an alternative to the current state-of-the-art trench vent design.

Due to the vent size constraints in current state-of-the-art hearing aid systems, a further embodiment of the present invention is to provide a feature which increases the available opening size for the vent, namely for the trench-type vent. This is depicted in FIG. 11, wherein the hearing aid's 1 ridge/key raised projection 1110 that runs longitudinally along the full length of the outer surface of the hearing aid (and opens at both the inner and outer ends of the hearing aid), projecting into and displacing the cartilage along that length, provides availability of space for provision of a trench 1120 that is formed or cut into the projection 1110 and if needed, even further down 1130 into the hearing aid's body (as shown). In the latter case, the present invention's trench 1120 "piggy-backs" the hearing aid's surface trench vent 1130, in that the ridge/key vent 1120 would coincide with the trench vent 1130 by sitting atop said trench vent 1130.

Figure 12:
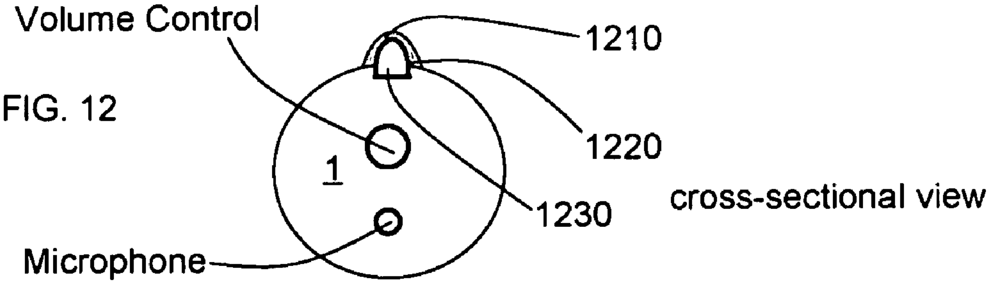
FIG. 12 is an end cross-sectional view of the present invention's ridge/key projection depicting its application in providing a hollow projection on the surface of a hearing aid to establish a vent or to enhance a hearing aid's existing trench vent.

Furthermore, an additional embodiment of the present invention is to provide a feature, which increases the available opening size for a vent, namely by providing a hollow ridge/key projection on the surface of the hearing aid or ear insert. This is depicted in FIG. 12, wherein the hearing aid's 1 (e.g., insertion element) ridge/key raised projection 1210 (e.g., protrusion) that runs longitudinally along at least a portion of the length of the outer surface of the hearing aid (and opens at both the inner and outer ends of the hearing aid), projecting into and displacing the cartilage along that length, is in the form of a hollow tube 1220, which provides for a vent 1230 through which air (and thus sound waves) can readily pass there through. This hollow tube 1220 can be used as the sole vent, or if additional vent area is needed, it can also be located above a trench vent 1230 that is recessed into the surface of the hearing aid 1.

It will be obvious to a person having ordinary skill in the art that the ridge/key projection described herein may be used singly, or with any combination of the above-described features of TMJ projections and venting systems.

At Least One Exemplary Embodiment

As to implementation of the ridges 40 and/or 50 in FIG. 1, one method is to add-on the ridge(s) to an existing hearing aid through the bonding of polymer or similar material to the appropriate location on the hearing aid's outer surface, namely, to comprise a longitudinal ridge 40 and/or 50 located along the ends of one or both of the major axes of the hearing aid's oval cross-section. To embody these ridges (e.g., protrusions) 40 and/or, one exemplary method using state-of-the-art materials is to apply a thin bead of light-curing, industry standard material to the intended path for the ridges 40 and/or 50 on the hearing aid, then cure this bead until it reaches solidification, and then to reapply and cure a second (and subsequent) layer if needed for increasing ridge height and/or thickness. Each application layer is typically about 0.030-inch thick, though other thicknesses may be applied depending upon the need at hand. A ridge height of about 0.050-inch more or less and a thickness range of about 0.040-inch to 0.070-inch will accommodate most users' ear canal anthropometry.

The longitudinal length of the ridge will be located only on that portion of the hearing aid, which interfaces with the outer, cartilaginous region of the ear canal. A length of 0.50-inch or less is typically sufficient. Those skilled in the art of manufacturing hearing aids (as well as other ear canal inserts such as custom-molded hearing protectors) will recognize that the dimensions provided herein are subject to the natural variability of human ear dimensioning, and then adjust accordingly. Another method of manufacturing the ridge(s) 40 and/or 50 is to determine the location of the ridge(s) in advance of the final casting of the hearing aid from the ear canal impression, and to form the ridge(s) as a part of that original casting, rather than adding them on later. Of course, computerized digital shell-making technology will greatly simplify the entire issue.

Adjustability

With either the add-on or original casting methods of implementing the ridge(s) 40 and/or 50 in FIG. 1, the dimensions (ridge height, thickness, and length) as well as the ridge(s) cross-sectional shape, can easily be adjusted after the original manufacture via application of a grinding wheel (or similar device) to precisely shape and fine-tune the ridge(s) such that it optimally interlocks with the ear canal of the given user. The manufacture and subsequent fine-tuning of such a ridge key system is not currently a recognized standard-of-practice for hearing aid manufacturers or dispensers; however, the methods for achieving this optimality of anthropometric fit are straightforward to those of ordinary skill in hearing aid art, and represent an important advancement in fitting technology and methodology, similar to the orthodontic practice of fitting dentures, or other impression-based bodily-mounted devices.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments.

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A non symmetrically collapsible in the circumferential direction in-the-ear-canal device comprising:

an insertion element; and at least one non-circumferential protrusion, where the at least one non-circumferential protrusion is operatively connected to a surface of the insertion element, where the at least one non-circumferential protrusion extends longitudinally along at least a portion of the insertion element, where the at least one non-circumferential protrusion is configured upon insertion to be positionable against the flesh of a user's outer, cartilaginous portion of the ear canal, said flesh covering an underlying subdermal cartilaginous region; where the at least one non-circumferential protrusion includes a material that is sufficiently incompressible with a volumetric dimension to displace said cartilage such that cartilage deforms and takes on the approximate geometric shape of the at least one non-circumferential protrusion; and where the at least one non-circumferential protrusion exerts a stabilizing force that facilitates insertion element maintaining a fixed position against said cartilaginous region.

2. The device according to claim 1 wherein the at least one non-circumferential protrusion terminates at one end of the insertion element before reaching the boney region that surrounds the inner portion of the ear canal and on the opposite end before reaching the opening of the ear canal.

3. The device according to claim 1 wherein the at least one non-circumferential protrusion has sufficient volumetric dimension to displace said cartilage causing flesh of ear canal to be stretched around the insertion element such that a seal between flesh and said insertion element is maintained during movements of the ear canal, said seal preventing acoustic feedback and preventing migration of sound around surface of said insertion element.

4. The device according to claim 1 wherein the at least one non-circumferential protrusion has sufficient volumetric dimension to displace said cartilage such that said insertion element is maintained as stable in a fixed position during movements of the ear canal.

5. The device according to claim 1 wherein the at least one non-circumferential protrusion has a portion of a cross section of at least one of a rounded, triangular, rectangular, cup-shaped, conical, or trapezoidal shape, along at least a portion of the at least one non-circumferential protrusion's length.

6. The device according to claim 1 wherein the at least one non-circumferential protrusion comprises an open trench pathway formed into and along its full length, said trench terminating at a first end, where the first end terminates before reaching the boney region that surrounds the inner portion of the ear canal and where said trench terminates at a second end opposite the first end, where the second end terminates at or external to the opening of the ear canal, said trench thereby providing an air vent pathway from the first end to the second end.

7. The device according to claim 6 wherein said open trench pathway aligns with and thus enlarges a preexisting trench vent that has been formed into said insertion element.

8. The device according to claim 1 wherein the at least one non-circumferential protrusion houses a hollow, open tube formed into the protrusion and along its full length, said tube terminating at a first end before reaching the boney region that surrounds the inner portion of the human ear canal and terminating at a second end at or external to the opening of the ear canal, said tube thereby providing an air vent pathway from its said first end to said second end.

9. The device according to claim 8 wherein said hollow, open tube pathway aligns with and thus enlarges a preexisting trench vent that has been formed into said insertion element.

10. The device according to claim 1 wherein the at least one non-circumferential protrusion is located on the lower (inferior) front (anterior) quadrant of the surface of said insertion element, that quadrant being the region which confronts the nearby temporomandibular joint, thereby applying pressure via the interceding cartilage between said projection and said joint, assisting in stabilizing the joint itself.

* * * * *